United States Patent [19]

Iwasaki et al.

[11] Patent Number: 5,424,446
[45] Date of Patent: Jun. 13, 1995

[54] PROCESS FOR PREPARING OPTICALLY ACTIVE 4-MERCAPTO-2-PYRROLIDONE DERIVATIVE AND INTERMEDIATE THEREFOR

[75] Inventors: Tameo Iwasaki, Nishinomiya; Kazuhiko Kondo, Osaka; Tadashi Nakatani, Takatsuki; Ryuzo Yoshioka, Mishima, all of Japan

[73] Assignee: Tanabe Seiyaku Co., Ltd., Osaka, Japan

[21] Appl. No.: 166,866

[22] Filed: Dec. 15, 1993

[30] Foreign Application Priority Data

Dec. 28, 1992 [JP] Japan .................. 4-348970

[51] Int. Cl.$^6$ ........................................ C07D 207/416
[52] U.S. Cl. ........................................ 548/544
[58] Field of Search ........................................ 548/544

[56] References Cited

U.S. PATENT DOCUMENTS 5,153,187 10/1992 Iwasaki et al. .................. 514/210

FOREIGN PATENT DOCUMENTS 337637 3/1989 European Pat. Off. .

OTHER PUBLICATIONS

Chemical Abstracts Iwasaki et al (1992) 117:212225m, 2-(2-Oxypyrroldin-3-ylthio)-6-(1-hydroxyethyl)-1-methylcarbapen-2-em-3-carboxylic acid pivaloyloxymethyl ester.

*Primary Examiner*—David B. Springer
*Attorney, Agent, or Firm*—Browdy and Neimark

[57] ABSTRACT

A process for preparing an optically active 4-mercapto-2-pyrrolidone derivative of the formula:

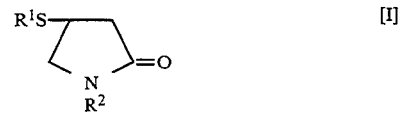

wherein a group of the formula: —SR$^1$ is a protected or unprotected mercapto group, and the group of the formula: =NR$^2$ is a protected or unprotected imino group, which comprises subjecting racemic 4-amino-3-mercaptobutyric acid or a salt thereof to optical resolution by using 1-(2,3,4-trichlorophenyl)ethanesulfonic acid, followed by subjecting the product to cyclization reaction after protecting the functional groups thereof, if necessary, and further optionally removing the protecting groups therefrom. The present process is industrially advantageous than conventional processes for preparing optically active 4-mercapto-2-pyrrolidone derivatives which are useful as an intermediate for various medicines such as carbapenem antibacterial agents.

7 Claims, No Drawings

PROCESS FOR PREPARING OPTICALLY ACTIVE 4-MERCAPTO-2-PYRROLIDONE DERIVATIVE AND INTERMEDIATE THEREFOR

The present invention relates to a novel process for preparing optically active 4-mercapto-2-pyrrolidone derivatives and optically active 4-amino-3-mercaptobutyric acid which is an intermediate for preparing the optically active 4-mercapto-2-pyrrolidone derivatives.

PRIOR ART

4-Mercaptopyrrolidone derivatives, especially optically active 4-mercapto-2-pyrrolidone derivatives are useful as an intermediate for various medicines, for example, they are well known as an intermediate for preparing 2-(2-oxo-4-pyrrolidinylthio)-6-(1-hydroxyethyl)-1-methylcarbapen-2-em-3-carboxylic acid, which is a carbapenem antibacterial agent [cf. Japanese Patent First Publication (Kokai) No. 49783/1990]. Moreover, 4-mercaptopyrrolidine-2-thione derivatives, which are prepared by thiocarbonylating 4-mercapto-2-pyrrolidone derivatives, are as well used for synthesis of carbapenem antibacterial agents [cf. Japanese Patent First Publication (Kokai) No. 279588/1992].

Hitherto, optically active 4-mercapto-2-pyrrolidone has been prepared by converting the hydroxy group of optically active 4-hydroxy-2-pyrrolidone into an active leaving group, followed by introducing a mercapto group into 4-position of the pyrrolidone nucleus by reacting the product with a thiolacetic acid [cf. Japanese Patent First Publication (Kokai) Nos. 49783/1990 and 279588/1992]. However, this process consists of several steps for preparing optically active 4-hydroxy-2-pyrrolidone, and the reagent used therein is expensive and is explosive, and hence, it has been desired to develop industrially advantageous process for preparing 4-mercapto-2-pyrrolidone.

Under the above circumstances, the present inventors have intensively studied, and found that racemic 4-amino-3-mercaptobutyric acid is effectively optically resolved by using optically active 1-(2,3,4-trichlorophenyl)ethanesulfonic acid to give novel optically active 4-amino-3-mercaptobutyric acid, from which there is easily obtained the desired optically active 4-mercapto-2-pyrrolidone derivatives by subjecting it to cyclization reaction, and have accomplished the present invention.

BRIEF DESCRIPTION OF THE INVENTION

An object of the present invention is to provide a novel process for preparing optically active 4-mercapto-2-pyrrolidone derivatives, which are useful as an intermediate for preparing medicines, said process being less expensive and more industrially advantageous than conventional processes.

Another object of the present invention is to provide a process for preparing optically active 4-amino-3-mercaptobutyric acid, which is an intermediate for preparing the optically active 4-mercapto-2-pyrrolidone derivatives.

DETAILED DESCRIPTION OF THE INVENTION

According to the present invention, optically active 4-amino-3-mercaptobutyric acid or a salt thereof is prepared by reacting racemic 4-amino-3-mercaptobutyric acid or a salt thereof with optically active 1-(2,3,4-trichlorophenyl)ethanesulfonic acid or a salt thereof to give two diastereomer salts of 4-amino-3-mercaptobutyric acid 1-(2,3,4-trichlorophenyl)ethanesulfonate, followed by separating a less-soluble diastereomer salt thereof from the other by using the difference of the solubility of two diastereomer salts, and if necessary, further by decomposing the separated salt. Moreover, according to the present invention, optically active 4-mercapto-2-pyrrolidone derivatives of the formula [I]:

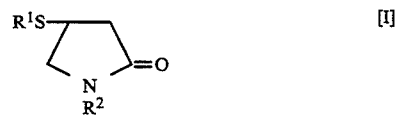

wherein a group of the formula: —SR$^1$ is a protected or unprotected mercapto group, and a group of the formula: =NR$^2$ is a protected or unprotected imino group, is prepared by subjecting the above obtained optically active 4-amino-3-mercaptobutyric acid, or a salt thereof, or said compound having a protected amino group and/or protected mercapto group, or a reactive derivative at the carboxyl group thereof, to cyclization reaction to give a compound of the formula [II]:

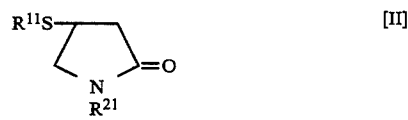

wherein a group of the formula: —SR$^{11}$ is a protected or unprotected mercapto group, and a group of the formula: =NR$^{21}$ is a protected or unprotected imino group, and when R$^{11}$ and/or R$^{21}$ is a protecting group, if necessary, followed by removing said protecting groups from the compound [II].

The optical resolution of racemic 4-amino-3-mercaptobutyric acid or a salt thereof is carried out by reacting with optically active 1-(2,3,4-trichlorophenyl)ethanesulfonic acid or a salt thereof in a suitable solvent, followed by collecting a resulting less-soluble diastereomer salt.

4-Amino-3-mercaptobutyric acid may be used either in the free form or in the form of a salt thereof. The salt includes, for example, a salt with mineral acids (e.g. hydrochloride, hydrobromide, sulfate, nitrate, hydrofluoride, etc.) or a salt with organic acids (e.g. methanesulfonate, p-toluenesulfonate, etc.). On the other hand, 1-(2,3,4-trichlorophenyl)ethanesulfonic acid may also be used either in the free form or in the form of a salt thereof. The salt includes, for example, metal salts (e.g. sodium salt, potassium salt, barium salt, etc.), or organic basic salt (e.g. an ammonium salt, a lower alkylamine salt, benzylamine salt, pyridine salt, etc.). When a metal salt is used, it is preferable to add a suitable amount of a mineral acid into a reaction system.

The solvent includes, for example, water, water-miscible organic solvents (e.g. a lower alkanol, acetonitrile, dioxane, etc.), or a mixture of these solvents.

The optical resolving reagent, 1-(2,3,4-trichlorophenyl)ethanesulfonic acid is used in an amount of 0.5 to 2.0 mole equivalents, preferably in an amount of 0.5 to 1 mole equivalent, to 1 mole equivalent of 4-amino-3-mercaptobutyric acid.

When 4-amino-3-mercaptobutyric acid is reacted with optically active 1-(2,3,4-trichlorophenyl)ethanesulfonic acid, the reaction solution may optionally be heated.

The precipitation of less-soluble diastereomer salt from the reaction solution is carried out either by allowing the reaction solution to stand or by stirring the reaction solution, or by seeding a crystal of the diastereomer salt into the reaction solution. The precipitation is carried out at a temperature from a solidifying point to a boiling point of the solvent to be used, but preferably at room temperature or with warming, for example, at a temperature from 0° C. to 100° C., preferably at a temperature from 20° C. to 50° C.

The crystals of the less-soluble diastereomer salt thus precipitated are collected by a conventional separation method such as filtration, centrifugation, and the like. The precipitated crystals are almost optically pure, and need no more purification, but the purity thereof can become higher by recrystallization.

The diastereomer salt may be converted into a free optically active 4-amino-3-mercaptobutyric acid by decomposition when necessary. The decomposition of the diastereomer salt is carried out by a conventional method, for example, by treating it with an acid or a base in a solvent. The acid includes, for example, mineral acids (e.g. hydrochloric acid, sulfuric acid, nitric acid, hydrobromic acid, etc.), strongly acidic cation-exchange resin, and the like. The base includes, for example, inorganic bases (e.g. an alkali metal hydroxide, an alkali metal oxide, an alkali metal carbonate, an alkali metal hydrogen carbonate, etc.), organic bases [e.g. ammonia, a lower alkylamine (methylamine, etc.), an aralkylamine (benzylamine, etc.)], strongly basic anion-exchange resin, and the like. The solvent includes, for example, water, a lower alkanol, acetonitrile, dioxane, or a mixture thereof. The decomposition reaction is carried out at a temperature from cooling to heating, preferably at ambient temperature, for example, at a temperature from 0° C. to 80° C., preferably at a temperature from 10° C. to 40° C.

After separating the desired optical isomer as mentioned above, the undesired antipode compound may be converted into racemic 4-amino-3-mercaptobutyric acid by subjecting said antipode compound to cyclization reaction with heating in acetic anhydride to give optically active 4-mercapto-2-pyrrolidone derivative [II] having the acetylated sulfur atom and the acetylated nitrogen atom, followed by elimination of the mercapto group of the optically active compound [II] and re-addition of a mercapto group to the resultant to give racemic 4-mercapto-2-pyrrolidone derivative [II], and further by subjecting the racemic compound [II] to hydrolysis. Thus, according to the present process there is theoretically quantitatively obtained optically active 4-amino-3-mercaptobutyric acid from racemic 4-amino-3-mercaptobutyric acid by repeating these steps.

The salt of 4-amino-3-mercaptobutyric acid used in the cyclization reaction is, for example, salts with mineral acids (e.g. hydrochloride, sulfate, nitrate, etc.) or salts with organic acids [e.g. 1-(2,3,4-trichlorophenyl)ethanesulfonate, etc.], and the like. When the 1-(2,3,4-trichlorophenyl)ethanesulfonate of 4-amino-3-mercaptobutyric acid is used in the cyclization reaction, the diastereomer salts obtained in the previous step is used as it is without decomposition.

The cyclization reaction of a free 4-amino-3-mercaptobutyric acid, a salt thereof, or said compound having a protected amino group and/or a protected mercapto group, is carried out in the presence of a condensing agent. The condensing agent includes, for example, dicyclohexylcarbodiimide, phosphorus pentachloride, phosphoryl chloride, thionyl chloride, and the like. The cyclization reaction of a reactive derivative at the carboxyl group of 4-amino-3-mercaptobutyric acid is carried out in the presence or absence of an acid acceptor. The reactive derivative at the carboxyl group thereof is, for example, an acid halide, a mixed acid anhydride, an active ester of 4-amino-3-mercaptobutyric acid. The acid acceptor includes, for example, an alkali metal hydroxide, an alkali metal carbonate, an alkali metal hydrogen carbonate, a tri-lower alkylamine, pyridine, and the like.

The cyclization reaction of 4-amino-3-mercaptobutyric acid is preferably carried out while protecting the mercapto group and/or amino group thereof. The protection of these groups may be carried out prior to the cyclization reaction, but the protection reaction of these functional groups and the cyclization reaction may be carried out simultaneously. The reagent used in this reaction may be any ones which can protect the mercapto group and the amino group and also can promote the cyclization reaction, especially an acylating agent may be preferable because it can function as an active esterifying agent for the carboxyl group as well. The acylating agent is, for example, an anhydride or halide of a lower alkylcarboxylic acid such as acetic acid, propionic acid, etc., or an arylcarboxylic acid such as benzoic acid, etc., and used in an amount of 3 to 10 mole equivalents, preferably 5 to 8 mole equivalents, to 1 mole equivalent of the starting 4-amino-3-mercaptobutyric acid.

When the amino group and/or the mercapto group of 4-amino-3-mercaptobutyric acid are protected prior to the cyclization reaction, the protecting group is preferably an acyl group such as acetyl group, palmitoyl group, benzoyl group, etc., or an aralkyl group such as benzyl group, 4-methoxybenzyl group, and the like.

The solvent used in the cyclization reaction may be any conventional inert solvents which do not affect the reaction, for example, dimethylformamide, toluene, dioxane, and the like. When the cyclization reaction and the protection of the functional groups of the starting compound are carried out simultaneously by using an acylating agent, the acylating agent can work as a solvent as well, and hence, no other solvent is necessary.

The reaction is carried out at room temperature or with heating, for example, at a temperature from 25° C. to 140° C., preferably at a temperature from 100° C. to 140° C.

The removal of these protecting groups after the cyclization reaction may be carried out by a conventional method such as acid-treatment, reduction, hydrolysis, etc., which should be selected according to the types of the protecting groups to be removed. When a protecting group is an acyl group, the protecting group is removed by acid-treatment or hydrolysis, for example, by adding 1 to 15% (especially 5 to 10%) hydrogen chloride-lower alkanol (methanol, etc.) solution to the compound [II], followed by stirring the mixture at room temperature.

When the compound [I] wherein the sulfur atom is protected is needed, for example, the product obtained in the above mentioned de-protection reaction is reacted with a protecting agent (e.g. an acylating agent)

to give the compound [I] wherein 4-mercapto group is selectively protected.

The 1-(2,3,4-trichlorophenyl)ethanesulfonic acid used in the optical resolution may be recovered after the decomposition of the diastereomer salt by a conventional method, for example, by using ion-exchange resin, etc. When optically active 4-amino-3-mercaptobutyric acid 1-(2,3,4-trichlorophenyl)ethanesulfonate is used in the cyclization reaction without decomposition, after the cyclization reaction, the reaction mixture is concentrated, and to the residue are added a solvent (e.g. toluene, etc.) and sodium acetate, and the mixture is heated, allowed to cool, and the precipitated crystals are collected by filtration to recover 1-(2,3,4-trichlorophenyl)ethanesulfonic acid in the form of a sodium salt thereof. In this procedure, the reaction product [II] may be obtained from the filtrate after separating the crystals. Moreover, an organic solvent (e.g. ethyl acetate, chloroform, etc.) and water are added to the residue obtained by concentration of the reaction mixture after the cyclization reaction, and thereby the mixture is separated into 1-(2,3,4-trichlorophenyl)ethanesulfonic acid in the aqueous layer and the reaction product [II] in the organic layer.

The optically active 4-mercaptopyrrolidone derivative [I] thus obtained is useful as an intermediate for introducing the side chain into carbapenem derivatives by a known method, for example, by the method disclosed in Japanese Patent First Publication (Kokai) No. 49783/1990 or 279588/1992. For instance, the optically active compound [I] may optionally be converted into the corresponding thioketone compound by treating it with a thiocarbonylating agent (e.g. phosphorus pentasulfide, Lawson reagent, etc.), and the optically active 4-mercaptopyrrolidone derivatives or a thioketone compound thereof is converted to the corresponding 1-methylcarbapenem derivative of the formula [VIII]:

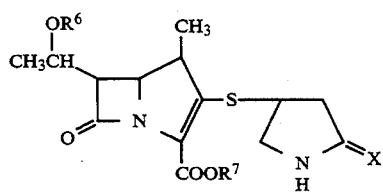

[VIII]

wherein a group of the formula: —$OR^6$ is a protected or unprotected hydroxy group, $R^7$ is hydrogen atom or an ester residue, and X is oxygen atom or sulfur atom, which is useful as an antibacterial agent, by reacting it with a reactive derivative at 2-oxo group of a ketone compound of the formula [VII]:

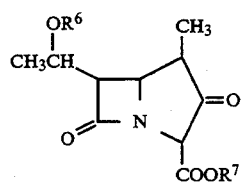

[VII]

wherein the group of the formula: —$OR^6$ and $R^7$ are the same as defined above, followed by removing the protecting group and/or the ester residue from the compound [VIII] when $R^6$ is a protecting group and/or $R^7$ is an ester residue which can be a protecting group for carboxyl group, and if necessary, further by converting the product into a pharmaceutically acceptable ester or salt thereof.

The starting racemic 4-amino-3-mercaptobutyric acid may be prepared by treating a racemic 4-hydroxy-2-pyrrolidone derivative of the formula [V]:

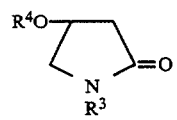

[V]

wherein a group of the formula: —$OR^4$ is a protected or unprotected hydroxy group, and a group of the formula: =$NR^3$ is a protected or unprotected imino group, with a base to eliminate the group of the formula: —$OR^4$ therefrom, to give a 3-pyrrolin-2-one derivative of the formula [IV]:

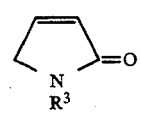

[IV]

wherein the group of the formula: =$NR^3$ is the same as defined above, followed by subjecting the compound [IV] to addition reaction with a thiol compound of the formula [VI]:

$R^4S$—H  [VI]

wherein a group of the formula: —$SR^5$ is a protected or unprotected mercapto group, to give a 4-mercapto-2-pyrrolidone derivative of the formula [III]:

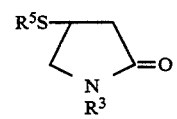

[III]

wherein the groups of the formulae: —$SR^5$ and =$NR^3$ are the same as defined above, and if necessary, by removing the protecting groups from the compound [III], and further by subjecting the product to hydrolysis.

When the groups of the formulae: =$NR^3$ and —$OR^4$ in the starting racemic 2-pyrrolidone derivatives [V] are a protected imino group or a protected hydroxy group, respectively, these groups may be ones protected by an acyl group such as acetyl group, palmitoyl group, benzoyl group, benzyloxycarbonyl group, and the like.

The elimination reaction of the group of the formula: —$OR^4$ from the compound [V] may be carried out in the presence of a base in a solvent. The base includes, for example, organic bases (e.g. a tri-lower alkylamine, pyridine, a di-lower alkylaniline, etc.), or inorganic bases (e.g. an alkali metal carbonate, an alkali metal hydrogen carbonate, etc.), and is used in an amount of 0.01 to 5 mole equivalents, preferably 0.05 to 2 mole equivalents, to 1 mole equivalent of the starting compound. The solvent may be any inert solvents which do not affect the reaction. The reaction is carried out at a temperature from cooling to heating, preferably at a temperature from 0° C. to 80° C., more preferably at a temperature from 20° C. to 40° C.

The thiol compound [VI] used in the addition reaction may be thiol compounds which may optionally be protected by an acyl group (e.g. acetyl group, palmitoyl group, benzoyl group, etc.) or an aralkyl group (e.g. benzyl group, 4-methoxybenzyl group, etc.). When a free thiol compound is used, it is used in an amount of 5 to 20 mole equivalents, preferably 10 to 15 mole equivalents, to 1 mole equivalent of the starting compound. When a protected thiol compound is used, it is used in an amount of 1 to 3 mole equivalents, preferably 1 to 1.5 mole equivalent, to 1 mole equivalent of the starting compound.

The addition reaction is carried out under the same temperature and in the same solvent as those for the above mentioned elimination reaction.

The removal of the protecting groups from the racemic, compound [III] thus obtained is carried out by a conventional method such as acid-treatment, reduction, etc., which is selected according to the types of the protecting groups to be removed. On the other hand, the ring-opening reaction by hydrolysis is preferably carried out in the presence of an acid or a base in a solvent. The acid includes, for example, mineral acids (e.g. hydrochloric acid, sulfuric acid, hydrobromic acid, etc.) or organic acids (e.g. trifluoroacetic acid, etc.), and the like. The base includes, for example, an alkali metal hydroxide, alkali metal carbonate, and the like. The solvent may be any inert solvents which do not affect the reaction, and the reaction is carried out at a temperature from cooling to heating, preferably at a temperature from 50° C. to 110° C., more preferably at a temperature from 80° C. to 100° C. When a protecting group for the sulfur atom or nitrogen atom is an acyl group, the acyl group is advantageously removed simultaneously with the ring-opening reaction.

The present optically active 1-(2,3,4-trichlorophenyl)ethanesulfonic acid is a novel compound, and can be prepared by the steps of subjecting 2′,3′,4′-trichloroacetophenone to reduction to give an alcohol compound, halogenating the alcohol compound to give 1-(2,3,4-trichlorophenyl)halogenoethane, converting it to racemic 1-(2,3,4-trichlorophenyl)ethanesulfonic acid with an alkali metal sulfite, followed by optically resolving it with optically active leucine. The racemic 2-pyrrolidone derivative [V] may be prepared by the method disclosed in Farmaco Ed. Sc., 33, 130 (1978).

Throughout the present description and claims, the "lower alkyl group" and the "lower alkanol" mean ones having 1 to 6 carbon atoms, and the "lower alkanoyl group" means ones having 2 to 7 carbon atoms.

EXAMPLES

The present invention is illustrated in more detail by the following Examples and Reference Example, but should not be construed to be limited thereto.

The optical purity in Examples is estimated by quantitatively determining each isomer with high performance liquid chromatography (HPLC) using a column for separating optical isomers.

Conditions for HPLC Analysis

Column: CROWNPAK CR (+) (manufactured by Daicel Chemical Industries, Ltd.)
Solvent: Aqueous perchloric acid solution (pH 1)
Flow Rate: 1.0 ml/minute
Detection: UV 210 nm
Temperature: 10° C.

Example 1

A mixture of racemic 4-amino-3-hydroxybutyric acid (50 g) and acetic anhydride (198 ml) is refluxed for 1.5 hour. After cooling, the reaction mixture is concentrated, and the resulting residue is subjected twice to azeotropic distillation with toluene. The resulting oily product (76 g) is dissolved in ethyl acetate (175 ml), and thereto is added triethyl amine (23.3 ml), and the mixture is allowed to stand at room temperature overnight. The ethyl acetate solution is cooled with ice, and thereto is added thiolacetic acid (33 ml), and the mixture is stirred at room temperature for three hours. The reaction solution is washed with water, dried, and evaporated to remove the solvent to give racemic 1-acetyl-4-acetylthio-2-pyrrolidone (79 g).

Yield: 93%

NMR (CDCl$_3$) δ: 2.36 (s, 3H), 2.50 (s, 3H), 2.5–2.7 (m, 1H), 3.1–3.2 (m, 1H), 3.7–3.8 (m, 1H), 4.0–4.3 (m, 2H)

Example 2

To racemic 1-acetyl-4-acetylthio-2-pyrrolidone (338 g) is added 6N hydrochloric acid (200 ml), and the mixture is refluxed for three hours. The mixture is cooled to room temperature, and washed with ethyl acetate, and the aqueous layer is concentrated under reduced pressure. The residue is subjected to azeotropic distillation successively with water, isopropanol and toluene, and the residue is crystallized from isopropanol. The crystals are collected by filtration, and dried to give racemic 4-amino-3-mercaptobutyric acid hydrochloride (156 g). This compound contains one molecular of isopropanol.

Yield: 54%

NMR (CDCl$_3$) δ: 1.15 (d, 6H, J=6.2 Hz), 2.6–3.1 (m, 3H), 3.3–3.5 (m, 2H), 3.9–4.1 (m, 1H)

Example 3

(−)-1-(2,3,4-Trichlorophenyl)ethanesulfonic acid (3.18 g) is dissolved in water (17.4 ml), and thereto is added aqueous solution of racemic 4-amino-3-mercaptobutyric acid hydrochloride (3.77 g) in water (24.6 ml). The mixture is dissolved at 70° C.–80° C., and allowed to cool. After cooling, the mixture is stirred under ice-cooling for one hour, and the precipitated crystals are collected by filtration, washed, and dried to give (3R)-4-amino-3-mercaptobutyric acid (−)-1-(2,3,4-trichlorophenyl)ethanesulfonate (3.8 g).

Yield: 40.4%
Optical purity: 96% e.e.
M.p. 153°–156° C.
[α]$_D^{25}$: −49.6° (c=1, methanol)
IR (KBr) cm$^{-1}$: 3488, 2940, 1732, 1651
NMR (DMSO-d$_6$+D$_2$O) δ: 1.48–1.52 (d, 3H, J=7.0 Hz), 2.46–3.34 (m, 5H), 4.36–4.47 (q, 1H, J=7.0 Hz), 7.56–7.69 (q, 2H, J=8.6 Hz)

Example 4

To (3R)-4-amino-3-mercaptobutyric acid (−)-1-(2,3,4-trichlorophenyl)ethanesulfonate (1.42 g) is added acetic anhydride (1.9 ml), and the mixture is heated at 70° C. for two hours. The reaction solution is concentrated, and the residue is subjected to azeotropic distillation with toluene, and thereto is added ethyl acetate. The organic layer is washed with water, dried, and evaporated to remove the solvent. The residue is crystallized from hexane, and the crystals are collected by filtration to give (+)-(4R)-1-acetyl-4-acetylthio-2-pyrrolidone (560 mg).
Yield: 83%
M.p: 49°–51° C.
$[\alpha]_D^{28}$: +48.3° (c=1, methanol)

Example 5

(+)-(4R)-1-Acetyl-4-acetylthio-2-pyrrolidone (6 g) is dissolved in 5% hydrogen chloride-methanol solution, and the mixture is stirred at room temperature for 25 minutes. The mixture is evaporated to remove the solvent, and the residue is subjected to azeotropic distillation with toluene. To the residue is added acetyl chloride (6 ml), and the mixture is stirred for 4.5 hours. The precipitated crystals are collected by filtration, and dissolved in chloroform. The chloroform solution is washed with water, dried, and evaporated to remove the solvent to give (4R)-4-acetylthio-2-pyrrolidone (3.8 g).
Yield: 81%
NMR(CDCl$_3$) δ: 2.29 (dd, 1H, J=6.3, 16 Hz), 2.35 (s, 3H), 2.80 (dd, 1H, J=8.8, 16 Hz), 3.31 (dd, 1H, J=6, 10 Hz), 3.88 (dd, 1H, J=6, 10 Hz), 4.10–4.23 (m, 1H), 6.99 (brs, 1 Hz)

Reference Example 1

(1) In methanol (284 ml) is suspended 2',3',4'-trichloroacetophenone (94.7 g), and thereto is added sodium borohydride (7.6 g) at 15° C.–25° C. The mixture is stirred at 25° C. for two hours, and evaporated to remove the methanol. To the residue is added 2N hydrochloric acid (110 ml), and the mixture is extracted with ethyl acetate. The organic layer is washed with water, dried, and evaporated to remove the solvent to give crude 1-(2,3,4-trichlorophenyl)ethanol (95 g).
M.p. 87°–89° C.
IR (Nujol) cm$^{-1}$: 3270, 1580, 1460
NMR (CDCl$_3$)δ: 1.46 (d, 3H, J=7.0 Hz), 5.15–5.40 (q, 1H, J=7.0 Hz), 7.26–7.60 (m, 2H)

(2) The above product (93 g) is dissolved in toluene (190 ml), and thereto is added dropwise phosphorus tribromide (48.7 g) at 20° C.–30° C. The mixture is stirred at the same temperature for one hour, and thereto is added water with cooling. The aqueous layer is extracted with toluene, and the combined organic layers are washed with water, dried, and evaporated to remove the solvent to give crude 1-(2,3,4-trichlorophenyl)bromoethane (124.2 g).
NMR (CDCl$_3$) δ: 2.02 (d, 3H, J=6.9 Hz), 5.52–5.63 (q, 1H, J=6.9 Hz), 7.39–7.53 (q, 2H, J=8.6 Hz)

(3) To the above product (124.2 g) are added water (280 ml) and sodium sulfite (94.7 g), and the mixture is stirred at 95° C.–100° C. for 20 hours. To the mixture is added water (900 ml), and the mixture is washed with ethyl acetate. To the aqueous layer are added conc. hydrochloric acid (107.5 ml) and water (1000 ml). The aqueous layer is heated at 70° C.–80° C., and thereto is added L-leucine (40.2 g), and the mixture is dissolved. The mixture is gradually cooled, and the precipitated crystals are collected by filtration, washed with cold water, and dried to give crude (−)-1-(2,3,4-trichlorophenyl)ethanesulfonic acid L-leucine salt monohydrate (59.4 g), which is crystallized twice from water to give (−)-1-(2,3,4-trichlorophenyl)ethanesulfonic acid L-leucine salt monohydrate (40.4 g).
Yield: 24% (calculated from 2',3',4'-trichloroacetophenone)
M.p. 231°–232° C.

IR (KBr) cm$^{-1}$: 3500, 2950, 1738, 1625
NMR (DMSO-d$_6$) δ: 0.90 (d, 6H, J=5.2 Hz), 1.35–1.90 (m, 6H), 3.78–4.00 (t, 1H, J=5.2 Hz), 4.20–4.40 (q, 1H, J=7.4 Hz), 7.55–7.80 (q, 2H, J=8.6 Hz), 8.00–8.40 (br, 3H)
$[\alpha]_D^{25}$: −32.4° (c=1, methanol)

(4) The above product (40.4 g) is dissolved in methanol, and the mixture is neutralized with 25% aqueous ammonia. The mixture is stirred at the same temperature for one hour, and the precipitated L-leucine is removed by filtration. The filtrate is concentrated, and the residue is dissolved in water, and the mixture is passed through the IR-120B (H+) strongly acidic cation-exchange resin (manufactured by ORGANO CORPORATION), and the column is washed with pure water. The eluate and washing are combined, and concentrated to give (−)-1-(2,3,4-trichlorophenyl)ethanesulfonic acid (26.5 g).
Yield: 99.4%
NMR (DMSO-D$_6$) δ: 1.54 (d, 3H, J=6.9 Hz), 4.30–4.60 (q, 1H, J=6.8 Hz), 7.53–7.83 (q, 2H, J=8.6 Hz)
Physical properties of (−)-1-(2,3,4-trichlorophenyl)ethanesulfonic acid sodium salt
M.p. 312°–318° C.
IR (KBr) cm$^{-1}$: 3480, 1640, 1440
NMR (DMSO-d$_6$) δ: 1.46 (d, 3H, J=6.9 Hz), 4.20–4.46 (q, 1H, J=6.8 Hz), 7.55–7.85 (q, 2H, J=8.6 Hz)
$[\alpha]_D^{25}$: −79.2° (c=1, water)

Reference Example 2

(+)-(4R)-1-Acetyl-4-acetylthio-2-pyrrolidone (3 g) and triethylamine (2.1 ml) are dissolved in ethyl acetate (30 ml), and the mixture is refluxed for three hours, and then allowed to stand at room temperature for 8 hours. To the reaction solution is added thiolacetic acid (1.2 ml), and the mixture is stirred at room temperature for 5 hours. The reaction solution is washed with water, dried, and evaporated to remove the solvent to give (±)-1-acetyl-4-acetylthio-2-pyrrolidone (2.7 g).

Reference Example 3

(4R)-4-Acetylthio-2-pyrrolidone (10 g) is dissolved in toluene (100 ml), and thereto is added gradually phosphorus pentasulfide (9.5 g), and the mixture is stirred at room temperature for 20 minutes. To the reaction solution are added water and ethyl acetate, and the mixture is stirred at room temperature for 1.5 hour. The insoluble materials are removed by filtration, and the organic layer is washed with water, dried, and evaporated to remove the solvent. The residue is recrystallized from toluene to give (+)-(4R)-4-acetylthiopyrrolidine-2-thione (7.9 g).
Yield: 72%
M.p. 94°–95° C.
$[\alpha]_D^{25}$: +57.7° (c=1, methanol)

EFFECTS OF THE INVENTION

According to the present invention, racemic 4-amino-3-mercaptobutyric acid can be effectively optically resolved to give optically active 4-amino-3-mercaptobutyric acid, and there is obtained in high yield optically active 4-mercapto-2-pyrrolidone derivative by subjecting optically active 4-amino-3-mercaptobutyric acid to cyclization reaction. Accordingly, by the present process there is obtained optically active 4-mercapto-2-pyrrolidone derivative less expensively and more

What is claimed is:

1. A process for preparing optically active 4-amino-3-mercaptobutyric acid or a salt thereof, which comprises reacting racemic 4-amino-3-mercaptobutyric acid or a salt thereof with optically active 1-(2,3,4-trichlorophenyl)ethanesulfonic acid or a salt thereof to give two diastereomer salts of 4-amino-3-mercaptobutyric acid 1-(2,3,4,-trichlorophenyl)ethanesulfonate, separating a less-soluble optically active diastereomer salt by using the difference of the solubility of two diastereomer salts, and if necessary, decomposing the separated salt.

2. A process for preparing racemic 4-amino-3-mercaptobutyric acid, which comprises:
treating a racemic 2-pyrrolidone derivative of the formula:

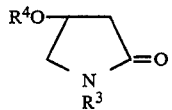

wherein $R^3$ is a hydrogen atom or a protecting group and $R^4$ is a hydrogen atom or a protecting group, with a base to give a 3-pyrrolin-2-one derivative of the formula:

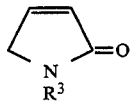

where $R^3$ is the same as defined above;
reacting the 3-pyrrolin-2-one derivative with a thiol compound of the formula:

$R^5S$—H wherein $R^3$ is a hydrogen atom or a protecting group to give a 4-mercapto-2-pyrrolidone derivative of the formula:

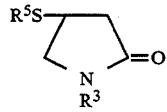

wherein $R^5$ and $R^3$ are the same as defined above;
if necessary, removing protecting groups from the 4-mercapto-2-pyrrolidone derivative; and
subjecting the product to hydrolysis.

3. A process for preparing an optically active 4-mercapto-2-pyrrolidone derivative of the formula (I):

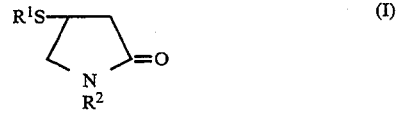

wherein $R^1$ is a hydrogen atom or a protecting group and $R^2$ is a hydrogen atom or a protecting group, which comprises:
preparing optically active 4-amino-3-mercaptobutyric acid, or a salt thereof, by means of a process in accordance with claim 1;
optionally reacting the product of said preparing step to introduce a protecting group $R^{21}$ into the amino group and/or to introduce a protecting group $R^{11}$ into the mercapto group and/or to introduce a reactive derivative at the carboxyl group thereof;
subjecting the product of said preparing and optionally reacting steps to a cyclization reaction to give a compound of the formula (II):

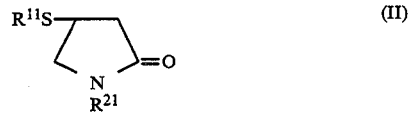

wherein $R^{11}$ is a hydrogen atom or a protecting group, and $R^{21}$ is a hydrogen atom or a protecting group, and when $R^{11}$ and/or $R^{21}$ are a protecting group, optionally removing said protecting groups from the product.

4. The process according to claim 2, wherein $R^3$ is a hydrogen atom or an acyl group, $R^4$ is a hydrogen atom or an acyl group and $R^5$ is a hydrogen atom or an acyl group or an aralkyl group.

5. The process according to claim 2, wherein $R^3$ is a hydrogen atom, acetyl group, palmitoyl group, benzoyl group or benzyloxycarbonyl group, $R^4$ is a hydrogen atom, acetyl group, palmitoyl group, benzoyl group or benzyloxycarbonyl group and $R^5$ is a hydrogen atom, acetyl group, palmitoyl group, benzoyl group, benzyl group or 4-methoxybenzyl group.

6. The process according to claim 3, wherein $R^2$ and $R^{21}$ are a hydrogen atom or an acyl group, and $R^1$ and $R^{11}$ are a hydrogen atom or an acyl group or an aralkyl group.

7. The process according to claim 3, wherein $R^2$ and $R^{21}$ are a hydrogen atom, acetyl group, palmitoyl group, benzoyl group or benzyloxycarbonyl group, and $R^1$ and $R^{11}$ are a hydrogen atom, acetyl group, palmitoyl group, benzoyl group, benzyl group or 4-methoxybenzyl group.

* * * * *